United States Patent [19]

Young

[11] 3,965,185

[45] June 22, 1976

[54] OXIDATION OF OLEFINS TO KETONES AND ALDEHYDES

[75] Inventor: Donald C. Young, Fullerton, Calif.

[73] Assignee: Union Oil Company of California, Brea, Calif.

[22] Filed: Apr. 11, 1974

[21] Appl. No.: 459,890

Related U.S. Application Data

[60] Division of Ser. No. 268,487, July 3, 1972, Pat. No. 3,850,990, which is a continuation-in-part of Ser. No. 775,150, Nov. 12, 1968, abandoned.

[52] U.S. Cl. .................. 260/586 P; 260/497 A; 260/590 R; 260/592; 260/597 B; 260/598; 260/599; 260/604 AC
[51] Int. Cl.² ................ C07C 45/04; C07C 27/12
[58] Field of Search ...... 260/586 P, 604 AC, 597 B, 260/497 A, 592, 598, 599, 590 R

[56] References Cited
UNITED STATES PATENTS

| | | | |
|---|---|---|---|
| 3,080,425 | 3/1963 | Smidt et al. | 260/586 P |
| 3,119,875 | 1/1964 | Steinmetz et al. | 260/604 AC |
| 3,122,586 | 2/1964 | Berndt et al. | 260/586 P |
| 3,149,167 | 9/1964 | Hornig et al. | 260/604 AC |
| 3,154,586 | 10/1964 | Bänder et al. | 260/586 P X |
| 3,288,845 | 11/1966 | Schaeffer | 260/604 AC |
| 3,290,362 | 12/1966 | Schaeffer | 260/604 AC |
| 3,301,905 | 1/1967 | Riemenschneider et al. | 260/597 B |
| 3,346,623 | 10/1967 | Young | 260/604 AC |
| 3,346,624 | 10/1967 | Schaeffer et al. | 260/604 AC |
| 3,346,626 | 10/1967 | Schaeffer et al. | 260/604 AC |
| 3,365,498 | 1/1968 | Bryant et al. | 260/604 AC |
| 3,370,073 | 2/1968 | Clement et al. | 260/586 P X |
| 3,384,669 | 5/1968 | MacLean et al. | 260/586 P X |
| 3,420,873 | 1/1969 | Olivier | 260/604 AC |
| 3,444,189 | 5/1969 | Olivier | 260/604 AC |
| 3,850,990 | 11/1974 | Young | 260/597 B |
| 3,859,336 | 1/1975 | Aquilo et al. | 260/604 AC |

*Primary Examiner*—Norman Morgenstern
*Attorney, Agent, or Firm*—Richard C. Hartman; Dean Sandford; Michael H. Laird

[57] ABSTRACT

Hydrocarbon olefins are oxidized to carbonyl compounds having the same number of carbon atoms by contacting the olefin with a Group VIII metal containing catalyst in the presence of ammonium nitrate which maintains the catalyst active for continuous conversion of the olefin to the carbonyl compound. Preferably, oxygen is also introduced to facilitate the oxidation and reduce the amount of ammonium nitrate consumed. In a specific embodiment, ethylene is oxidized to acetaldehyde by contacting an aqueous solution containing about 20 percent ammonium nitrate and catalytic amounts of palladium, present as a soluble salt or a complex, at a temperature of about 80°C. and at a pressure from about 1 to about 100 atmospheres.

7 Claims, No Drawings

OXIDATION OF OLEFINS TO KETONES AND ALDEHYDES

This is a division of Ser. No. 268,487, filed July 3, 1972, now U.S. Pat. No. 3,850,990, which is a continuation-in-part of Ser. No. 775,150, filed November 12, 1968, now abandoned.

DESCRIPTION OF THE INVENTION

The oxidation of hydrocarbon olefins using a Group VIII noble metal catalyst is well known and commercial processes for the production of acetaldehyde from ethylene have been developed. In these processes, an aqueous hydrochloric acid solution of palladous and cupric chlorides is contacted with ethylene and oxygen. The palladous chloride is an oxidant, however, since it is from 6,500 to 10,000 times more costly than acetaldehyde, it must be used catalytically. The cupric chloride serves as a redox agent which maintains the palladous chloride in its oxidized and active state while oxygen is introduced to maintain the cupric chloride in its oxidized state. While the aforementioned oxidation shows excellent selectivity for conversion of ethylene, some difficulty is experienced in applying the oxidation to higher olefins and to the oxidation of internal olefins, e.g., oxidation of cyclohexene or oxidation of octene. The latter olefins have a significantly lower reactivity and discourage attempts at oxidation. The reaction medium conventionally employed with this Group VIII noble metal oxidation is also highly corrosive and has required the use of expensive corrosion resistant materials such as titanium-lined vessels. Even when vapor phase processing is attempted, volatile halides from the catalyst cause corrosion problems in the vapor effluent lines. Finally, some difficulties are encountered with the stability of the solution since the oxidation of ethylene forms oxalic acid which precipitates the cupric salts used as redox agents in the solution as insoluble cupric oxalate and thereby deactivates the oxidation.

It is an object of this invention to provide a process exhibiting a relatively high reactivity for the oxidation of higher molecular weight olefins.

It is also an object of this invention to provide a process for the oxidation of olefins to carbonyl compounds under non-corrosive conditions.

It is a further object of this invention to provide a process for the oxidation of olefins to carbonyl compounds that is not dependent upon the use of a multivalent metal redox agent.

Other and related objects will be apparent from the following description of the invention.

I have discovered that ammonium nitrate functions as an oxidant to maintain Group VIII metals in oxidized states, i.e., in their higher valencies so that a continuous process for the conversion of olefins to carbonyl compounds can be achieved. The process comprises contacting the olefin with a Group VIII metal catalyst in the presence of ammonium nitrate. I have also found that, optionally, oxygen can be incorporated in the reaction mixture to facilitate this oxidation of an olefin.

The oxidation of this invention can be illustrated by the following equations using ethylene as a model olefin reactant and ammonium nitrate.

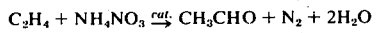

I.

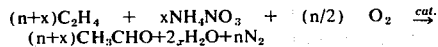

II.

While the equations offer a convenient presentation of the net reaction, it should be understood that the exact mechanism, which involves the participation of the Group VIII metal catalyst, is very complex and is not known with certainty.

The first reaction, however, summarizes the oxidation which occurs in the absence of any added oxygen wherein the ammonium nitrate serves as the sole oxidant for conversion of the olefin to the aldehyde product. In the second reaction, oxygen is also introduced and reduces the requirements for consumption of ammonium nitrate. In these oxidations, the oxidant can be converted substantially to nitrogen and water; however, some oxidation to nitrous oxide and nitrogen dioxide can occur with these gases being swept from the reaction zone before their complete reduction.

The catalyst for the oxidation process is a Group VIII metal which can be present in a liquid phase reaction medium in soluble form, e.g., as a salt or as a complex, so that homogeneous catalysis can be practiced. Alternatively, heterogeneous catalysis with a solid catalyst that can comprise the Group VIII metal as a solid salt, oxide, metal or complex, used alone or distended on a suitable solid support, can be practiced using liquid or vapor phase conditions. The Group VIII metals that can be used include iron, cobalt, nickel, platinum, rhodium, ruthenium, osmium, iridium and palladium. The Group VIII noble metals are preferred, and of these palladium is most preferred, because of its demonstrated greater activity. The metal can be incorporated in the reaction medium or on the solid catalyst in any desired form; it can be added in the metallic state; as the oxide; or as a salt, e.g., a halide such as ferric chloride, cobalt nitrate, nickel sulfate, palladium chloride, rhodium chloride, ruthenium bromide, iridium iodide, osmium bromide, chloroplatinic acid, etc.; or as the nitrate, sulfate, phosphate or a salt of the lower molecular weight ($C_1$–$C_5$) alkanoic acids, e.g., acetate, propionate, valerate, isobutyrate, etc. The metal can also be added as a complex with various ligands such as the nitroso complex or halo complexes and any of these can be used as the metal catalyst source. Complexes involving ligands with two or more complexing sites spaced in sufficient proximity to form a ring structure with the metal are chelates and a chelate of a Group VIII metal and a conventional metal chelating agent can be used such as the metal complexes with $C_4$ to about $C_{15}$ aliphatic or aromatic, 1,3-diketones such as acetylacetone, propionylacetone, butyrolactone, nonanoylacetone, benzoylacetone, naphthoylacetone, dibenzoylacetone, etc.

Examples of suitable halo complexes include ammonium tetrachloroferrate, ammonium hexafluoroferrate, potassium hexafluororuthenate, sodium hexachloroosmate, lithium hexachloriiridate, chloroplatinic acid, sodium fluoropallate, etc. Examples of suitable nitroso complexes include palladium nitroso chloride, sodium hexanitritocabalate, tris-triphenylphosphine nitroso rhodium, tris-triphenylarsine nitroso rhodium, tris-triphenylphosphine nitroso iridium, rhodium nitroso bromide, potassium nitridochloro osmiamate, etc.

Examples of other sources of the preferred Group VIII noble metals include:

bis(triphenylphosphite)iridium carbonyl chloride; tris(triphenylphosphite)iridium carbonyl hydride; iridium carbonyl; iridium tetrabromide, iridium tribromide, iridium trifluoride; iridium trichloride; osmium trichloride; chloroosmic acid; palladium hydride; palladous chloride, palladous cyanide; palladous iodide; palladous nitrate, platinic acid; platinous iodide; palladium cyanide; sodium hexachloroplatinate; potassium trichloro(ethylene) platinate(II); chloropentaaminorhodium(III)chloride; rhodium dicarbonyl chloride dimer; rhodium nitrate; rhodium trichloride; tris(triphenylphosphite)rhodium carbonyl hydride; tris(triphenylphosphite)rhodium(I)chloride; ruthenium trichloride; tetraaminorutheniumhydroxychlorochloride; etc.

The Group VIII metal is used in catalytic quantities relative to the olefin converted since once it is present in a sufficient amount for adequate contacting with the reactants, any further concentration of the metal has no effect on the reaction rate or total conversion. Accordingly, large quantities of olefin are converted, relative to the amount of Group VIII metal, e.g., at least about 100 moles per mol of Group VIII metal. Preferably at least about 1000 and, most preferably, at least about 10,000 moles of olefin are converted per mol of Group VIII metal used. The amount of the metal can comprise from 0.001 to about 5 weight percent of the liquid reaction medium in homogeneous catalysis or of the solid support when using heterogeneous catalysis. Preferably the amount is from 0.1 to 3.0 and, most preferably, from 0.5 to 2.0 weight percent.

It is believed that the Group VIII metal is maintained as a complex in the aqueous solution with hydroxo, aquo, nitroso and nitrato ligands. The complex is most stable at acidic pH values, e.g., from 2 to about 6, preferably from about 3 to 5, and it is believed that the acidity of the solution functions by limiting hydroxo ligands for the Group VIII metal. Any strong mineral acid can be used as the acid to reduce the solution pH, e.g., nitric, hydrohalic such as hydrochloric, hydrobromic, hydroiodic, hydrofluoric, sulfuric, etc. The amount of acid employed is that required to impart the aforestated pH values to the solutions and this is generally from about 1 to about 15 weight percent of the solution. The acid is not consumed during the reaction so it need not be added during the olefin oxidation.

The reaction can be practiced using homogeneous liquid phase or heterogeneous vapor phase catalysis. In the homogeneous liquid phase catalysis, any of the aforementioned sources of the Group VIII metal catalyst which are soluble in the liquid reaction medium can be dissolved therein. The reaction medium should also contain ammonium nitrate. Aqueous solutions can be used and are preferred for liquid phase processing; however, if desired, the lower ($C_1$–$C_5$) alkanoic acids can also be used as reaction media. Examples of these are formic, acetic, propionic, butyric, isobutyric, valeric, pivalic, isovaleric, etc. When heterogeneous processing is employed using either a liquid or vapor phase, the catalyst can be distended on a suitable inert solid carrier and the supported catalyst can be employed as a heterogeneous solid that is placed in a reactor as a compact bed of solids or suspended in the reactant stream as a dilute suspension or as a fluidized bed.

Any support or carrier which is a solid and inert to the reaction can be used such as titania, zirconia, alumina, silica, etc., or combinations of these materials. Examples include alumina, silica stabilized alumina containing from 1 to 15 percent silica as described in U.S. Pat. No. 2,437,532, the aluminum silicates, clay, naturally occurring or synthetically prepared zeolites such as chabazite, gnelenite or faujasite, as well as synthetic zeolites. The latter materials are partially dehydrated crystalline compositions of silica and alumina and contain quantities of one or more exchangeable cations such as sodium, potassium, hydrogen, magnesium, calcium, etc. The compositions and their preparation are described in U.S. Pat. Nos. 2,882,243 and 2,882,244. These compositions are characterized by crystal pores of relatively uniform pore diameter between about 5 and 14 Angstrom units. Several crystal forms of such molecular sieves are available and suitable for use herein as the carrier for the catalyst, redox agent and cocatalyst components of my invention including the "X", "Y", "L" and "J" crystal types. The sieves can be treated prior to deposition of the aforementioned catalytic metals by ion exchanging the monovalent alkali metal cation with a divalent metal. Also the sieves can be "decationized" by ion exchange with an ammonium salt followed by heating to decompose the zeolitic ammonium ion and leave a hydrogen ion. Any of the aforementioned carriers can be impregnated by the Group VIII metal by treatment with appropriate aqueous solutions of salts of the Group VIII metals.

The catalyst particle size can vary over wide limits from about 0.5 inch to about 1 micron average diameter. The particle size selected depends on the type of solid-vapor contacting employed in the reaction zone. A disperse gas phase reaction would employ the very fine particles passing about a 325 mesh screen. Use of a fluidized bed reactor would require use of particles passing a 20 but retained on a 400 mesh screen. Packed bed reactors, which are preferred, would use the larger diameter particles having diameters from 0.05 to 0.5 inch, preferably from about 0.1 to 0.25 inch. The specific surface of the catalyst can also vary widely, from about 10 to 800 square meters per gram.

The Group VIII metal component of the catalyst when distended on a solid carrier can be employed in an amount from about 0.01 to about 25 weight percent of the final catalyst. Preferably the metal is employed in a concentration from about 0.5 to about 10 weight percent based on the final catalyst. The metal can be distended on the carrier by impregnation of the carrier with a solution of a salt, complex or chelate of the metal. The impregnation can be achieved by evaporating the solvent from the admixture of inert carrier and catalyst solution or by addition of a precipitating agent to form an insoluble salt or hydroxide of the metal. The catalyst is thereafter dried and can be used in the reaction.

The hydrocarbon olefin oxidized in accordance with my invention can comprise any olefin having from 2 to about 20 carbons, preferably from 2 to about 10 carbons. The olefin has the following structure:

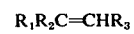

$R_1R_2C=CHR_3$ wherein $R_1$, $R_2$ and $R_3$ are hydrogen, or the same or different alkyl having from 1 to about 18 carbons or aryl having from 6 to about 10 carbons; or wherein one of said $R_1$, $R_2$ and $R_3$ together form a single alkylene group having from 2 to about 8 carbons.

Examples of useful olefins are the hydrocarbon olefins such as ethylene, propylene, butene-1, butene-2, 2-methylbutene-1, cyclobutene, cyclopentene, pentene-1, hexene-1, hexene-2, cyclohexene, 3-ethylhexene-1, isobutylene, octene-1, 2-propylhexene-1, ethylcyclohexene, decene-1, cycloheptene, cyclooctene, octene-2, cyclononene, 4,4'-dimethylnonene-1, dodecene-1, undecene-3, 6-propyldecene-1, tetradecene-2, 7-amyldecene-1, oligomers of olefins such as propylene tetramer, ethylene trimer, etc., hexadecene-1, 4-ethyltridecene-1, octadecene-1, 5,5-dipropyldodecene-1, vinylcyclohexane, allylcyclohexane, styrene, p-methylstyrene, alpha-methylstyrene, p-vinylcumene, beta-vinylnaphthalene, 1,1-diphenylethylene, allylbenzene, 6-phenylhexene-1, 1,3-diphenylbutene-1, 3-benzylheptene-1, o-vinyl-p-xylene, m-methylstyrene, divinylbenzene, 1-allyl-4-vinylbenzene, p-ethylstyrene, etc.

When the ammonium nitrate is continuously supplied to the reaction zone using either liquid or vapor phase processing and using gaseous, liquid or solid oxidant sources, it can be supplied at a rate approximately equal to its rate of consumption in the reaction. As indicated in the aforementioned equations (I) and (II), this requires approximately equal molar equivalents, generally from 0.9 to about 1.25 molar equivalents, of ammonium nitrate per mol of converted olefin when the oxidation is performed in the absence of oxygen and a varied amount, approximately 0.05 to 0.9 molar equivalents per mol of converted olefin when oxygen is also introduced. For economic processing, it is preferred to introduce oxygen and minimize the amount of ammonium nitrate consumed and, accordingly, it is preferred to consume sufficient ammonium nitrate to maintain the Group VIII metal in a stable, oxidized state. The preferred amount of ammonium nitrate consumed with oxygen introduction is from 0.1 to about 0.5 moles per mol of olefin converted. In general, the ammonium nitrate can be continuously supplied at a rate from 0.1 to 5.0 molar equivalents per mol of reactant olefin; preferably from 0.3 to 1.5 molar equivalent per mol of reactant olefin.

When the ammonium nitrate is incorporated in the reaction medium of a liquid phase process it can comprise from 5 to about 90 weight percent of the liquid phase. The ammonium nitrate can be employed in the solvent at any concentration from about 5 weight percent up to and exceeding its saturation in the particular solvent. In such case, the reaction solvent can contain a suspension of the ammonium nitrate. Accordingly, concentrations from about 5 to 90 weight percent of the liquid phase can comprise the ammonium nitrate or, preferably, from 5 to about 75 percent, and most preferably, from about 10 to about 50 weight percent.

In vapor phase processing, the ammonium nitrate can be introduced as a solid into the reaction zone, e.g., when a packed or fixed bed reactor is employed the ammonium nitrate can be dispersed throughout the bed as distinct particles intermixed with the catalyst particles bearing the platinum group metal. In suspension processing, the ammonium nitrate can be used as finely divided particles of the particle size previously described for the catalyst and can be admixed in the suspension with this catalyst. In fluidized bed processing the ammonium nitrate in finely divided form can be introduced as a suspension in the reactive vapors and carried into the fluidized bed for conversion in the reaction zone. In this process, the ammonium nitrate can be supplied, as needed, in a continuous fashion to the reaction zone.

In vapor phase processing, the reactant olefin and, optionally oxygen, can be introduced into the reaction zone in vapor phase suitably by admixing the proper proportions of the reactants with the aid of an inert diluent gas if desired. Relative ratios of the oxygen to olefin can be from about 1 to 100 to about 1:5 molar parts of oxygen per mol of the olefin. If desired, suitable inert diluents such as nitrogen, carbon dioxide, etc., can be introduced with the reactants and, if desired, air can serve as a suitable source of the oxygen. When reacting the higher molecular weight olefins, e.g., olefins having greater than about 10 carbon atoms, these reactants are preferably oxidized in liquid phase processing with a homogeneous catalyst or heterogeneous catalyst.

In liquid phase processing, the lower molecular weight gaseous olefins can be introduced as vapors, together with the oxygen, when employed, and the higher molecular weight olefins can be introduced as liquids into contact with the catalyst and the oxidant mixture in the reaction zone. When operating in a continuous fashion, a portion of the liquid phase can be continuously removed and the carbonyl products purified therefrom by suitable steps such as fractional distillation or azeotropic distillation of the liquid. The catalyst and remaining reaction solvent with any residual, dissolved quantities of the ammoniacal and nitrogen oxide compounds can then be recycled to further conversion in the reaction zone.

The products from a vapor phase reaction are, of course, recovered from the vapor effluent. Condensation of the vapor effluent and subsequent distillation or azeotropic distillation can be practiced to purify the desired carbonyl products.

When employing a liquid phase reaction zone, the products can also be continuously stripped or vaporized from the reaction zone and removed in a vapor effluent and thereafter condensed and fractionated to obtain the desired carbonyl products. The latter procedure would be of particular application to preparation of the lower molecular weight carbonyls, i.e., those containing less than about 10 carbon atoms.

If desired, batch or discontinuous processing can also be employed. With liquid phase processing, the reactants can be charged to the liquid phase reaction medium without the withdrawal of product therefrom and continuing reaction until a sufficient accumulation of product has occurred in the reaction zone to warrant discontinuing the reaction and recovering the product therefrom by the aforementioned techniques.

The reaction is performed under relatively mild conditions including temperatures from about 20° to 300°C., preferably from 50° to 150°C. and at pressures from 1 to 1000 atmospheres; preferably 1 to 100 atmospheres; and most preferably from 5 to 50 atmospheres. The desired temperature can be maintained in the reaction zone by conventional cooling techniques using indirect heat transfer or by direct heat transfer using the introduction of a volatilizable liquid as a quenching step for the exothermic reaction.

The invention will now be described by the following specific modes of practice thereof:

EXAMPLE 1

To a one-liter, three-necked flask is charged 500 grams acetic acid, 60 grams ammonium nitrate, 1 gram palladium metal, 10 grams lithium acetate and 15 milliliters nitric acid. The liquid mixture is heated to about 80°C. and the palladium metal dissolves and forms a clear, bright orange solution. The liquid is then heated to reflux temperature with stirring and ethylene is slowly introduced into the solution through a dispersion tube while maintaining the temperature constant at the reflux condition, i.e., 111°C. During the introduction of the ethylene, the color of the solution gradually turns dark. The reaction is continued for a period of several hours during which the effluent from the water cooled condenser is passed through dry ice traps and a liquid condensate is collected. Upon completion of the reaction period the products in the dry ice trap are analyzed and found to comprise chiefly acetaldehyde with a trace of vinyl acetate.

EXAMPLE 2

The flask is charged with 500 grams of 57 weight percent aqueous ammonium nitrate solution, 16 grams nitric acid and 1 gram palladium metal. The flask contents are heated to 100°C. and maintained at that temperature while 8 milliliters additional nitric acid is slowly introduced with stirring. After about 5 minutes the palladium metal is dissolved and the solution is a dark orange color. The temperature is lowered to 80°C. and ethylene is introduced into the solution through a gas dispersion tube. Upon introduction of the ethylene, the color of the solution darkens. The temperature is increased to 88°C. and the color is restored to the dark orange. The vapor effluent from the flask is passed through a water cooled condenser in the reflux position and then through 3 dry ice traps. The liquid collected in the dry ice traps is combined and analyzed to reveal that it is 95 percent acetaldehyde and 5 percent methyl nitrate.

EXAMPLE 3

The flask containing the catalyst solution from the preceding example is heated to 85°C. and then propylene is slowly introduced through the gas dispersion tube. Upon introduction of the propylene, the solution turns black. The temperature is raised to 87°C. and the solution is observed to return to the orange color. The condensate collected in the dry ice traps is analyzed by infrared and found to comprise acetone and propylene in equal weight amounts.

EXAMPLE 4

The flask is charged with 500 grams of a 57 weight percent ammonium nitrate aqueous solution and 16 grams nitric acid and the solution is heated to 90°C. and 1 gram palladium metal is added while stirring. The flask contents are stirred for 2½ hours at 105°C. and an additional 2 grams nitric acid is added and the solution is maintained with stirring at reflux temperature for 3 hours. The temperature of the solution is then adjusted to 70°C. and 50 milliliters cyclohexene is introduced and the color immediately turns black and metallic palladium is observed to precipitate from the solution. The temperature is raised to the reflux temperature, 76°C., and the palladium is observed to slowly dissolve into solution with the evolution of nitrogen. A portion of the flask contents is sampled and analyzed and found to contain cyclohexanone.

When the reaction is repeated with the substitution of 65 milliliters of octene-1, a similar reaction is observed and the product of the oxidation is octanal-2.

EXAMPLE 5

The flask is charged with 546 grams of an aqueous 57 weight percent ammonium nitrate solution and heated to 60°C. To the flask is then added 9 grams nitric acid and a total of 45 grams ferrous sulfate was slowly added while the temperature of the solution was raised to reflux, 110°C. When the ferrous sulfate is dissolved, ethylene is slowly introduced over a 30 minute period and the effluent gas is passed through a trap to recover acetaldehyde which is identified as a product of the oxidation.

EXAMPLE 6

A solid catalyst is prepared by impregnating approximately 100 grams of solid pellets comprising 10 percent silica and 90 percent alumina with an aqueous solution containing 5 grams palladium chloride. The pellets are 3/16-inch long by 3/16-inch diameter and are dried under vacuum for about 4 hours at 100°C.

The catalyst pellets are packed into a U-shaped glass tube fitted with gas introduction and withdrawal tubes at opposite ends and the tube is immersed in a heating bath maintained at a constant 165°C.

A vapor mixture of equal volumes of ethylene, ammonia and nitric oxide is passed through the glass tube and the vapor effluent is passed through several dry ice-cooled traps and acetaldehyde is recovered as the major product.

When the experiment is repeated with the addition of oxygen to the vapor mixture in approximately an equal volume proportion to each of the other components, simillar oxidation to acetaldehyde occurs.

EXAMPLE 7

The relative rates of oxidation of palladium in solutions of nitric acid and ammonium nitrate were determined. Air or oxygen was not introduced into contact with the solutions, however, the relative rates of oxidation observed in the experiment are also observed when oxygen is introduced into contact with the solutions as a supplemental oxidizing agent. The experiments were performed by adding 1.09 and 1.11 grams of palladium metal powder to 702 grams of an aqueous solution containing 400 grams ammonium nitrate and 63 grams nitric acid and to a solution containing only 63 grams nitric acid, respectively. The solutions were in one-liter laboratory flasks and were held at ambient temperature for 20 minutes and then were placed on a steam table. Samples of the solutions were withdrawn and the temperature of the solutions noted at 5, 20, 30, 45, 60, 120, 180 and 240 minutes after addition of the palladium metal.

Gas was observed to be evolved immediately upon the addition of the palladium to the ammonium nitrate solution while none was observed to be evolved from the nitric acid solution. The palladium completely dissolved in the ammonium nitrate solution after 90 minutes. After four hours most of the palladium was undissolved in the nitric acid solution. The concentrations, in weight of palladium found dissolved in the samples were as follows:

| Sample | Time | Temperature | Dissolved Palladium Concentration(ppm) | |
|---|---|---|---|---|
| | | | Nitric Acid | Ammonium Nitrate |
| 1 | 5 min. | Ambient | 7.4 | 14.8 |
| 2 | 20 | Ambient | 13.3 | 22.9 |
| 3 | 30 | 41–45°C. | 19.9 | 199 |
| 4 | 45 | 52–55°C. | 23.2 | 1028 |
| 5 | 60 | 60–61°C. | 27.9 | 1484 |
| 6 | 120 | 62–66°C. | 38.0 | — |
| 7 | 180 | 62°C. | 39.2 | — |

-continued

| Sample | Time | Temperature | Dissolved Palladium Concentration (ppm) Nitric Acid | Ammonium Nitrate |
|---|---|---|---|---|
| 8 | 240 | 62°C. | 42.0 | — |

The preceding experiments illustrate the significantly greater rate of oxidation of palladium in solution of ammonium nitrate than in nitric acid.

While the preceding examples serve to illustrate presently contemplated best modes of practice, it is not intended that the examples be construed as unduly limiting of the invention that is described and claimed herein.

I claim:

1. The method of oxidizing a hydrocarbon olefin having 2 to about 20 carbons to a carbonyl product thereof having the same number of carbon atoms as said olefin and selected from ketones and aldehydes which comprises contacting said olefin and molecular oxygen in a liquid reaction medium selected from the group consisting of aqueous media, $C_1$ to $C_5$ alkanoic acid media and combinations thereof, having dissolved therein a catalytic amount of a Group VIII noble metal containing catalyst and about 0.1 to about 5.0 moles of ammonium nitrate per mole of said olefin under reaction conditions including a pH of about 2 to about 6, a temperature of 25° to about 300°C. and a pressure of about 1 to about 1000 atmospheres sufficient to convert said olefin to said carbonyl product in an amount greater than 100 moles of said carbonyl product per mole of said Group VIII metal and consume about 0.05 to about 0.9 moles of said ammonium nitrate per mole of said olefin converted.

2. The method of claim 1 wherein said olefin has from 2 to about 10 carbons and said liquid medium contains about 5 to about 75 percent ammonium nitrate.

3. The method of claim 2 wherein said catalyst consists essentially of a Group VIII noble metal containing catalyst and said oxidation is conducted in the absence of any multivalent metal other than said Group VIII noble metal.

4. The method of claim 2 wherein said Group VIII metal is selected from platinum and palladium and said oxidation is conducted in the absence of any multivalent metal other than said platinum and palladium.

5. The method of claim 1 wherein said liquid medium contains about 0.5 to about 5.0 weight percent of said catalyst, and said catalyst is a noble metal salt soluble in said solution.

6. The method of claim 1 wherein said liquid medium contains about 0.5 to about 5.0 weight percent of a soluble salt of palladium or platinum and nitric acid, and said reaction of said olefin and oxygen is conducted under said reaction conditions sufficient to consume at least about 0.1 mole of ammonium nitrate per mole of olefin oxidized during said oxidation.

7. The method of claim 1 wherein said oxidation is conducted in the presence of said liquid medium comprising an aqueous or $C_1$–$C_5$ alkanoic acid solution containing about 10 to about 50 percent ammonium nitrate in the presence of a catalyst consisting essentially of a Group VIII noble metal containing catalyst in the absence of any other multivalent transition metal or compound thereof.

* * * * *